United States Patent
Beurer

(10) Patent No.: US 10,823,318 B2
(45) Date of Patent: Nov. 3, 2020

(54) CABLE TIE

(71) Applicant: Xenios AG, Heilbronn (DE)

(72) Inventor: Matthias Beurer, Stuttgart (DE)

(73) Assignee: XENIOS AG, Heilbronn (DE)

( * ) Notice: Subject to any disclaimer, the term of this patent is extended or adjusted under 35 U.S.C. 154(b) by 0 days.

(21) Appl. No.: 16/308,035

(22) PCT Filed: Apr. 27, 2017

(86) PCT No.: PCT/DE2017/000115
§ 371 (c)(1),
(2) Date: Dec. 7, 2018

(87) PCT Pub. No.: WO2017/211334
PCT Pub. Date: Dec. 14, 2017

(65) Prior Publication Data
US 2019/0309884 A1    Oct. 10, 2019

(30) Foreign Application Priority Data
Jun. 10, 2016   (DE) .................. 10 2016 007 091

(51) Int. Cl.
| F16L 33/035 | (2006.01) |
| B65D 63/10 | (2006.01) |
| A61M 39/12 | (2006.01) |
| F16L 33/02 | (2006.01) |
| H02G 3/32 | (2006.01) |

(52) U.S. Cl.
CPC ........... *F16L 33/035* (2013.01); *A61M 39/12* (2013.01); *B65D 63/1018* (2013.01); *F16L 33/02* (2013.01); *B65D 2563/108* (2013.01); *H02G 3/32* (2013.01)

(58) Field of Classification Search
CPC ............ A61M 39/12; B65D 2563/108; B65D 63/1018; F16L 33/02; F16L 33/035; H02G 3/32
See application file for complete search history.

(56) References Cited

U.S. PATENT DOCUMENTS

| 381,426 A | 4/1888 | Sargent |
| 3,197,164 A | 7/1965 | Hansen |
| 4,191,334 A * | 3/1980 | Bulanda ................. F16L 3/233 24/16 PB |

(Continued)

FOREIGN PATENT DOCUMENTS

| CN | 101859991 A | 10/2010 |
| CN | 101946110 A | 1/2011 |

(Continued)

OTHER PUBLICATIONS

International Search Report of PCT/DE2017/000115, dated Sep. 26, 2017.

(Continued)

*Primary Examiner* — Robert Sandy
*Assistant Examiner* — David M Upchurch
(74) *Attorney, Agent, or Firm* — Collard & Roe, P.C.

(57) ABSTRACT

A cable tie has a head piece and a strap, which can be pushed into the head piece, thereby fixing itself in a latching manner, wherein a wedge-shaped compensation piece, which can be positioned in the region of the head piece, is threaded onto the strap in order to bound a hollow space together with the strap.

13 Claims, 5 Drawing Sheets

(56) References Cited

U.S. PATENT DOCUMENTS

Figure 1:
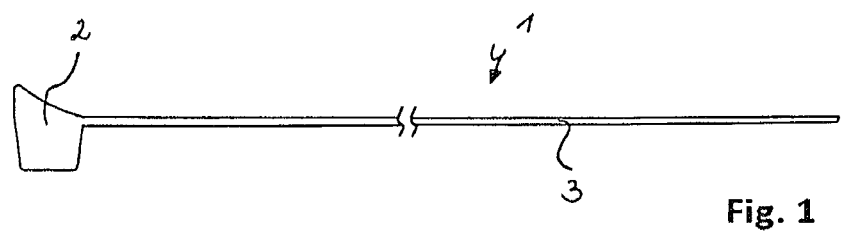

| | | | | |
|---|---|---|---|---|
| 5,224,244 A | * | 7/1993 | Ikeda | F16L 3/233 |
| | | | | 24/16 PB |
| 5,690,522 A | | 11/1997 | Moreau | |
| 9,828,152 B2 | | 11/2017 | Dinh | |
| 10,400,917 B2 | * | 9/2019 | Kitago | B65B 27/06 |
| 2003/0034171 A1 | * | 2/2003 | Joseph | F16L 3/233 |
| | | | | 174/135 |
| 2009/0211061 A1 | * | 8/2009 | Cianciolo | B65D 63/1072 |
| | | | | 24/16 PB |
| 2012/0210541 A1 | | 8/2012 | Koncelik, Jr. | |
| 2013/0081232 A1 | * | 4/2013 | Magno, Jr. | B65D 63/1063 |
| | | | | 24/16 PB |
| 2014/0165339 A1 | | 6/2014 | Yuan | |
| 2016/0325897 A1 | * | 11/2016 | Kierstead | H02G 3/30 |
| 2017/0297794 A1 | * | 10/2017 | Rollier | B65D 69/00 |

FOREIGN PATENT DOCUMENTS

| | | |
|---|---|---|
| CN | 105508739 A | 6/2014 |
| CN | 1038633699 A | 6/2014 |
| EP | 2 247 882 B1 | 2/2013 |
| WO | 00/00407 A1 | 1/2000 |

OTHER PUBLICATIONS

First Office Action in Chinese Patent Application No. 201780049320.8 dated Mar. 30, 2020 with Search Report.

* cited by examiner

CABLE TIE

CROSS REFERENCE TO RELATED APPLICATIONS

This application is the National Stage of PCT/DE2017/000115 filed on Apr. 27, 20017, which claims priority under 35 U.S.C. § 119 of German Application No. 10 2016 007 091.9 filed on Jun. 10, 2016, the disclosure of which is incorporated by reference. The international application under PCT article 21(2) was not published in English.

The invention relates to a cable tie, a set having such a cable tie, and a compensation piece for a cable tie.

Cable ties are also referred to as cable straps or ratchet strips and form a universally applicable, quick to use and inexpensive connection element.

Cable ties were originally designed to fix various cables and wiring harnesses to each other or to other objects. Cable ties are also used in the construction industry, however, for provisional assembly, as a packaging aid or in police work for restraining people. The invention also relates to special cable ties with moulded-on mounting elements such as adhesive sockets, anchor bolts or fir tree bases, such as are used in the automobile industry.

According to the invention cable ties are made of plastics, in particular PA 6.6 or PVC. Polyamide 6.6, which is also known as Nylon®, has proved a particularly advantageous material for cable ties. The cable ties can also be made from other materials, however, such as polyurethane, POM, ABS, PP, PE, PC, PEEK, other plastics, metal, aluminium casting or even high-grade steel.

In the case of disposable cable ties, internal or external teeth are used to ensure that the cable ties cannot be released. They can normally only be opened again by destroying them. In the case of cable ties with a plastic locking strap it is usually possible to unlock them with a needle which allows the loop to be undone. In order to produce cable ties with a particularly high tensile force, a metallic tongue is incorporated in the head, which enables the cable tie to be sealed by cutting the tongue into the body of the cable tie.

Reusable cable ties can be opened again by unlocking and thus are able to be used more than once. In addition, there are also cable ties with an open tie-head, double-head cable ties and cable ties with a special label area.

The invention relates to all cable ties of these types and in particular to the use of cable ties for fastening a hose to a section of pipe. This fastening is widely used in medical technology for fastening tubes supplying fluids, in particular blood or gases, to a hose connector, i.e. A tube or a tube coupling. The hoses, which are made of flexible material, are pressed on to the tube section using the cable tie in such a way that a sealed connection is produced.

A particular problem that arises in this application area is that the hose material may shrink slightly or lose its elastic properties, due to ageing or sterilization. This reduces the contact pressure between the hose and the tube section and this can lead to leakage problems. In practice, the first leaks usually arise in the area of the head of the cable tie, in which the cable tie does not lie flat on the hose connector. It has therefore been suggested that the cable tie head be shaped in such a way that the cable tie is in contact with the hose over as much of its circumferential surface as possible.

These cable ties have the disadvantage, however, that a special cable tie must be provided for each hose diameter. This increases the costs involved in the production of a single cable tie, and as the cable ties are usually produced in an injection moulding process, different moulds must be provided.

Cable ties with a head piece and a strap that can be pushed into the head piece and thereby fixed in place, wherein a compensation piece that can be positioned in the area of the head piece is threaded onto the strap in order to bound a hollow space with the strap, are known from U.S. Pat. No. 5,690,522 and EP 2 247 882 B1, for example.

The object of the invention therefore is to further develop a cable tie such that it provides a reliable contact pressure, which deforms an object which is compressed by the cable tie as evenly as possible around the circumference.

This object is achieved by means of a cable tie sensor having the features of claim 1.

According to the invention it is therefore proposed to combine a known cable tie with a compensation piece, which is threaded onto the cable tie. This compensation piece allows cheap, known cable ties produced in large quantities to be used, and at the same time a cable tie to be provided, which is optimally adapted to a specific application.

The compensation piece has a wedge-shaped cross section in the plane of the perimeter of the hollow space, with two long arms and a short base. The two long arms can therefore form a wedge between the head piece and the enclosed hollow space, while the short base facilitates the movement of the compensation piece on the strap. The strap then extends perpendicular to the long arms and is movable in an opening in the compensation piece and then through the opening in the head piece.

A surface which forms a long arm is designed planar as an abutment for the head piece. This causes a contact surface to be formed, which also enables a small amount of movement of the surfaces towards each other.

Such compensation pieces are inexpensive to manufacture and can be combined with known cable ties. This makes it possible, in particular, to combine inexpensive, injection moulded standard cable ties with an individual compensation piece, which due to its shape, choice of material and/or colour is optimally adapted to a specific purpose.

The compensation piece can be placed at any point on the strap of the cable tie. When the cable tie is in use it rests against the head piece of the cable tie. The two-part construction of head piece and compensation piece leads to the fact that the compensation piece is optimally positioned when the cable tie is tightened, and in the event of vibration or a change in the shape of the materials, the position of the compensation piece on the strap or relative to the head piece can only change slightly. As a result, the contact pressure can be maintained for longer.

Advantageous configurations are the subject matter of the dependent claims.

In particular for pressing a hose onto a piece of tubing, it is proposed that the compensation piece has a concave surface on its side facing the hollow space. Such a concave surface can fill the "gusset" between the head piece and the strap, in order to enlarge the contact surface. Depending on the application, in place of a concave surface a planar surface or a structured surface can also be provided, since an elastic hose material adapts to the shape of the surface.

If the strap bounds a circular hollow space, the concave surface of the compensation piece can approximately match the radius of the circular hollow space. In this context, approximately means a deviation of the radii of the compensation piece from the radius of the circumscribed hollow space by a maximum of +/−30%, and preferably a maximum of +/−10% and particularly preferably a maximum of +/−1%.

A very commonly used application in the field of medical technology is the fastening of hoses with a diameter of ⅜ inch and ¼ inch. It is therefore proposed that the concave surface approximately corresponds to the surface of a hose with a diameter of ⅜ inch or ¼ inch.

On its side facing the hollow space, the concave surface adjoins both the strap and the head piece. A shoulder, for example with a size of 0.5 mm to 5.0 mm, can be either on one of these sides or on both sides. This shoulder facilitates the production of the compensation piece and by providing the shoulder, which can also be rounded, it is possible to avoid sharp edges which in the event of improper use as a cutting surface, could damage a hose.

The handling properties of the compensation piece are improved if the junction between a surface forming a long arm with a surface forming the base is rounded off. Preferably, both junction surfaces are slightly rounded.

An unclaimed embodiment provides that the contact surface is designed such that during the contact it produces a centring of the surfaces relative to each other. This is achieved by means of a concave surface, for example, which fits into a convex surface. In addition, on this contact surface a structure can be provided between the head piece and the compensation piece to restrict the ability of the surfaces to move relative to each other.

A simple threading of the compensation piece onto the strap is achieved by the compensation piece being provided with a rectangular slot for receiving the strap, the longer side of which corresponds to the width of the strap, so that it can be displaced on the strap and does not slip off the strap. The compensation piece can therefore be moved by means of a slight pressure on the strap moveable and does not slip off the strap under its own weight. A compensation piece designed in such a way is also essential to the invention even without the characterizing features of patent claim 1.

It is particularly advantageous if the compensation piece has a rectangular slot for receiving the strap, the shorter or longer side of which has a resilient or elastic contact surface, so that this contact surface presses against the strap. This ensures that even after repeated use of the compensation piece, the compensation piece does not accidentally slip off the strap.

The compensation piece can have a stop, which interacts with a counterpart on the strap. This stop ensures that the compensation piece can be placed onto the strap only as far as a certain position. This stop can also be, for example, part of a locking device in the compensation piece, so that the position on the stop can be changed in a tactile manner.

Because in the course of time the strap of the cable tie can be extended, the locking device in the head piece may yield, or the object surrounded by the strap, such as a hose line, may shrink, it is advantageous even in this case if a fixed contact pressure is maintained. This is achieved by the compensation piece either being or having an elastic part, which deforms when compressed. This can ensure, for example, that the compensation piece remains in contact with the hose even if the hose were to shrink by around one or more millimetres in diameter. Therefore, the elasticity need not be provided on the strap or on the head piece, but instead an elasticity in a part of the compensation piece or else a compensation piece made of an elastic material can provide the necessary elasticity in order to maintain an adequate contact pressure of the strap on the material surrounded by the strap.

For this purpose the compensation piece can have an elastic contact surface, in particular on the side facing the hollow space, that forms a pressure pad. The compensation piece can also, however, be formed of a more flexible material than the head piece with the strap, in order to achieve the spring action.

The elasticity can also be achieved by means of a special structure on the contact surfaces of the strap. This may be achieved, for example, by providing indentations or corrugations, which bend under compression.

In order to produce a cable tie that is optimized for specific hose diameters, it is proposed to provide a set consisting of such a cable ties and a hose section, or to offer specific pieces of hose with a cable tie and compensation piece specially matched thereto.

Since such compensation pieces can be used with any known cable ties, such a compensation piece may be offered as a proposed extension. This compensation piece can be produced as an injection moulded part and preferably as a two-component injection moulded part. The two-component injection moulded part allows functionally different areas during an injection moulding process, such as resilient contact surfaces and stable forming regions, to be produced from different materials. For producing smaller quantities and for multi-component manufacturing, the use of a 3D-printing process is proposed.

If the compensation piece has a wedge-shaped cross section, the shorter arm can have a label or an imprint. In addition, different compensation pieces can be produced in different colours.

Figure 2:
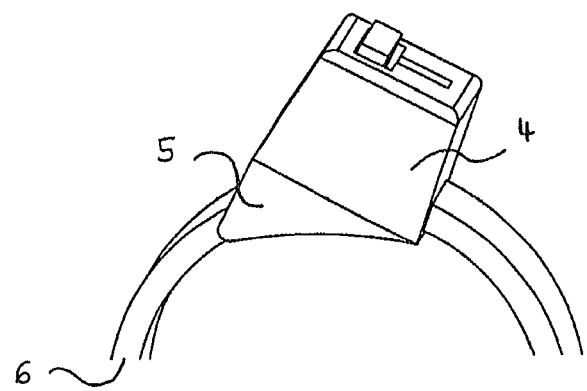
Figure 3:
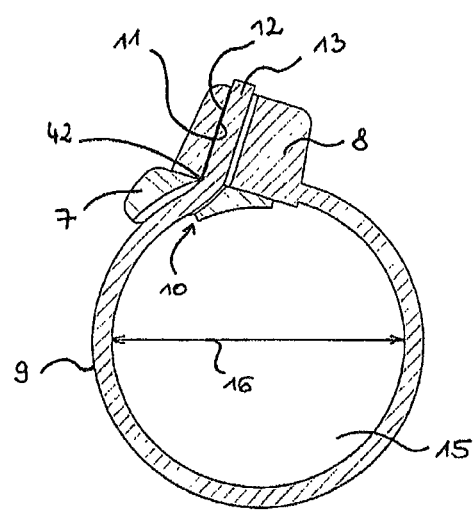
Figure 4:
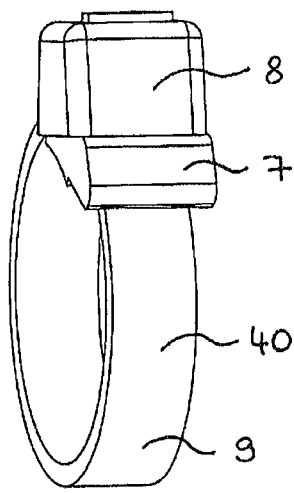
Figure 5:
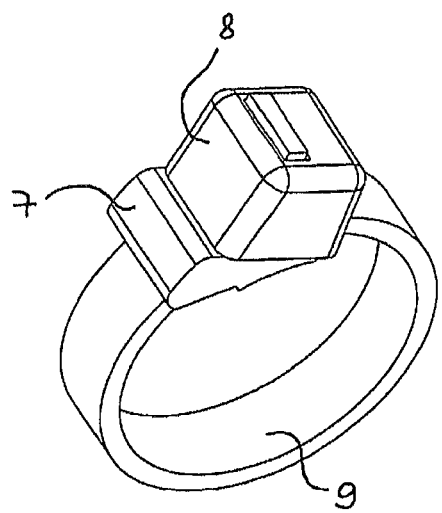
Figure 6:
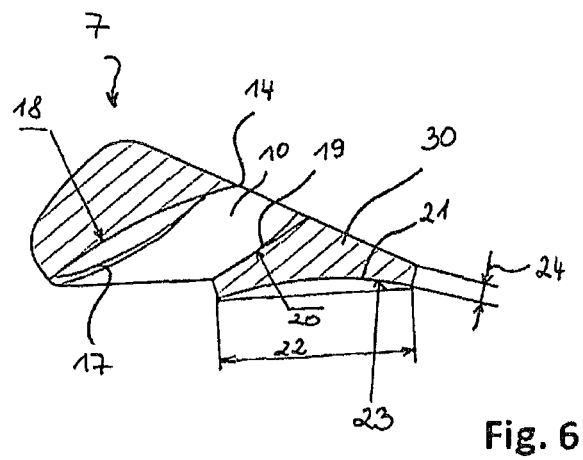
Figure 7:
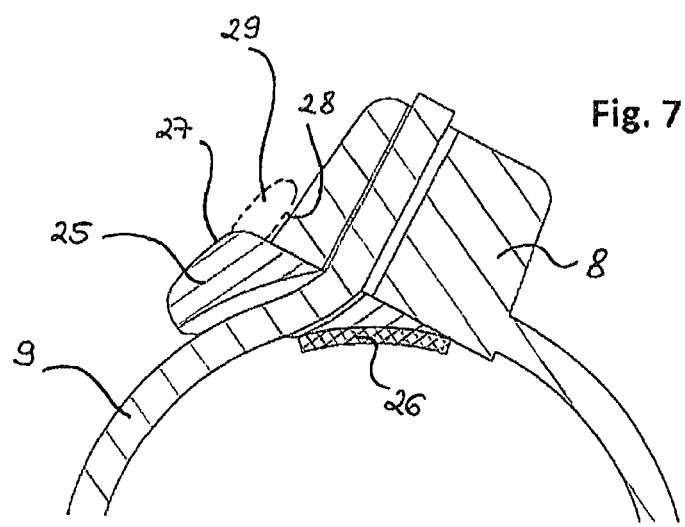
Figure 8:
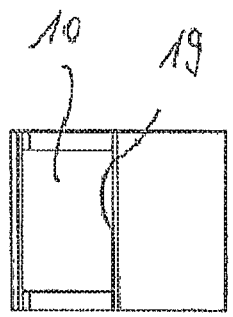
Figure 9:
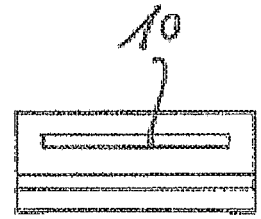
Figure 10:
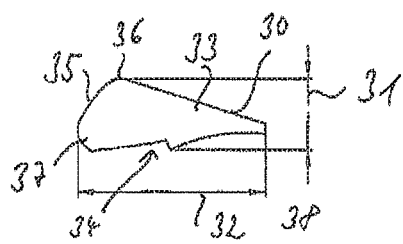
Figure 11:
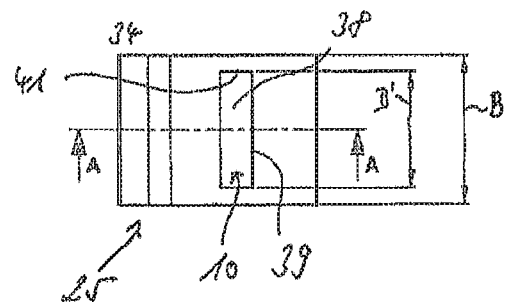
Figure 12:
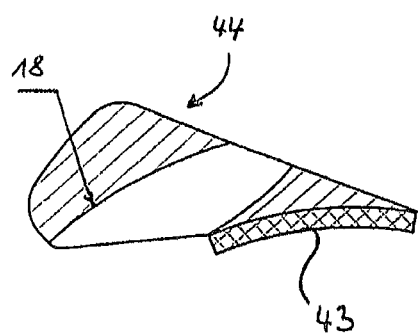
Figure 13:
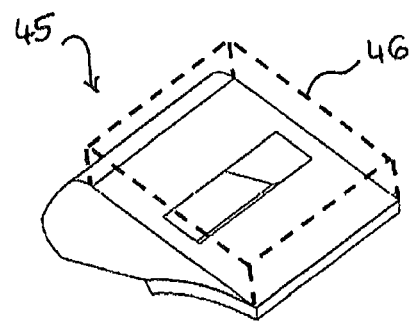
Figure 14:
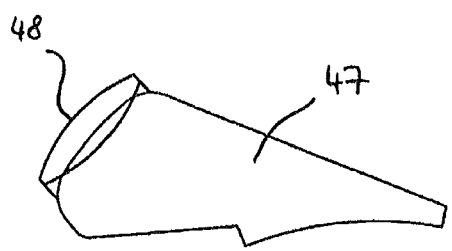

Different design variants of cable ties and compensation pieces are shown in the drawings and are explained in more detail below. Shown are:

FIG. 1 a schematic representation of a section through a known cable tie,

FIG. 2 a perspective view of a cable tie with compensation piece,

FIG. 3 a section through a cable tie with a compensation piece,

FIG. 4 a first perspective view of the cable tie shown in FIG. 3,

FIG. 5 a second perspective view of the cable tie shown in FIG. 3,

FIG. 6 the compensation piece as shown in FIG. 3 as a detail,

FIG. 7 a partial section of a cable tie with a compensation piece, which has a flexible contact surface, FIG. 8 a front view shown in FIG. 7 on the compensation piece, FIG. 9 a rear view of the compensation piece shown in FIG. 7, FIG. 10 a side view of the compensation piece shown in FIG. 7, FIG. 11 a plan view of the compensation piece shown in FIG. 7, FIG. 12 a view of a section through the compensation piece shown in FIG. 7, FIG. 13 a perspective view of a compensation piece according to FIG. 7 with an implied elastic support, and FIG. 14 a compensation piece as shown in FIG. 7 with an implied printable plate.

The cable tie 1 shown in FIG. 1 consists of a head piece 2 and a strap 3.

In the exemplary embodiment shown in FIG. 2, a compensation piece 5 is in contact with the head piece 4 and the strap 6 has been pulled through the compensation piece 5 and the head piece 4. A similar design is shown by the exemplary embodiment according to FIG. 3. Here, the compensation piece 7 is in contact with the head piece 8 and the strap 9 has been threaded through an opening 10 in the compensation piece 7 and through the head piece 8. A set of teeth 11 on the head piece 8 interacts with a set of teeth 12 on the strap 9 in order to hold the end 13 of the strap 9 in the head 8.

In addition, the edge 14 on the compensation piece 7 can interact with the teeth 12 on the strap 9. However, this is not necessary for the functioning of the invention.

In the exemplary embodiment shown in FIG. 3, the hollow space 15 bounded by the strap 9 is circular with a diameter 16 of ⅜ inch. In a matching manner to this exemplary embodiment, FIG. 6 shows the compensation piece 7 with a concave or convex outer contact surface 17 on the opening 10, with a radius 18 of, for example, 10.7 cm. The opposite surface 19 is designed concave with a radius 20 of, for example, 7.0 cm. The contact surface 21 facing the hollow space 15 has a length 22 of 4.6 mm and a radius 23 of 8.3 cm. As the shoulder 24, on both sides of the contact surface 21 a height of 0.5 mm is provided.

FIG. 7 shows the interaction of the head piece 8 and the strap 9 with a compensation piece 25, which has a flexible contact surface 26, which is preferably elastic. The flexibility ensures a planar contact, for example with a piece of hose (not shown) arranged in the hollow space 15 and an elasticity compensates for any reduction in the contact pressure due to an elongation of the strap 9 or a shrinking of the hose piece.

An enlarged labelling area 27 and an additional contact surface 28 of the compensation piece 25 on the head piece 8 is obtained by the projection 29 on the compensation piece 25.

Cumulatively or as an alternative to the flexible surface 26, in the region 30 between the compensation piece 7 and the head piece 8 or in the region of the surface 19 between the compensation piece 7 and the strap 9, a flexible and preferably elastic surface (not shown) can also be provided, in order to exert adequate long-lasting pressure on the component (not shown) surrounded by the cable tie.

These flexible contact surfaces can also be designed as a shoulder.

The compensation piece 25 can have, for example, a height 31 of 3.5 mm, a length 32 of 9.1 mm and a width B of 7 mm. The wedge-shaped cross section is formed by two long arms 33, 34 and a short base 35.

Each of the junctions 36 from the long arm 33 to the short base 34 and that 37 between the long arm 34 to the short base 35 is rounded off. The contact surface 30 of the long arm 33 for the contact with the head piece 8, on the other hand, is flat.

As a through passage 10 for the strap 9, the compensation piece 25 has a slot 38, the longer side 39 of which having a width B' in the exemplary embodiment of 5.5 mm matches the width 40 of the strap 9, so that the compensation piece 25 can be displaced on the strap 9 and does not slip off the strap 9.

The shorter side 41 of the slot 38 has an elastically designed contact surface, which presses against the strap 9 and thus forms a slight resistance when the compensation piece 25 is moved along the strap 9.

The edge 14 shown in FIG. 6 forms a stop 42 on a toothed outer surface 12 of the strap 9 and interacts with the strap 9 as a counterpart.

FIG. 12 shows an elastic part 43 on the compensation piece 44, which can deform under pressure and ensures a good contact of the compensation piece 44 against an object which is surrounded by the strap 9.

A compensation piece 45 with an elevation 46, implied by dotted lines, designed as a preferably elastic contact surface of the compensation piece 45 against a head 8 of the cable tie, is shown in FIG. 13.

FIG. 14 shows a compensation piece 47 with an enlarged contact surface 48 on the short base of the compensation piece. This surface is suitable for marking or affixing a label.

The invention claimed is:

1. A cable tie having a head piece and a strap, which can be pushed into the head piece, thereby fixing itself in a latching manner, wherein a compensation piece, which can be positioned in the region of the head piece, is threaded onto the strap in order to bound a hollow space together with the strap,
   wherein the compensation piece has a wedge-shaped cross section in the plane of the perimeter of the hollow space, the compensation piece comprising a first long side facing the headpiece, a second long side facing the hollow space and a short base side, wherein the first long side has a first distal end and a second distal end, the first distal end and the second distal end defining a flat planar surface extending from the first distal end to the second distal end, an entirety of which flat planar surface abuts the head piece.

2. The cable tie according to claim 1, wherein the second long side has a concave surface.

3. The cable tie according to claim 2, wherein the strap bounds a circular hollow space and the concave surface approximately corresponds to the radius of the circular hollow space.

4. The cable tie according to claim 2, wherein between the concave surface and the head piece a shoulder is provided.

5. The cable tie according to claim 2, wherein a shoulder is provided between the concave surface and the strap.

6. The cable tie according to claim 1, wherein a transition from the surface which forms at least one of the first long side and the second long side is rounded off towards the surface which forms the short base side.

7. The cable tie according to claim 1, wherein the compensation piece has a rectangular slot for receiving the strap,
   wherein the strap has a width, and
   wherein the slot has a longer side corresponding to the width of the strap, so that the slot can be displaced on the strap and does not slip off the strap.

8. The cable tie according to claim 1, wherein the compensation piece has a rectangular slot for receiving the strap,
   wherein the slot has a shorter side and a longer side, and
   wherein the shorter or the longer side has a resilient or elastic contact surface that presses against the strap.

9. The cable tie according to claim 1, wherein the compensation piece has a stop, which interacts with a counterpart on the strap.

10. The cable tie according to claim 1, wherein the compensation piece is or comprises an elastic part, which deforms under compression.

11. A set comprising the cable tie according to claim 1 and a piece of tubing.

12. The cable tie according to claim 1, wherein the compensation piece is a molded part.

13. A cable tie having a head piece and a strap, which can be pushed into the head piece, thereby fixing itself in a latching manner, wherein a compensation piece, which can be positioned in the region of the head piece, is threaded onto the strap in order to bound a hollow space together with the strap, wherein the compensation piece has a wedge-shaped cross section in the plane of the perimeter of the hollow space, with two long arms and a short base, and a surface, which forms a long arm is designed planar as an abutment for the head piece, wherein the compensation piece has a rectangular slot for receiving the strap, wherein the slot has a shorter side and a longer side, and wherein the shorter or the longer side has a resilient or elastic contact surface that presses against the strap.

* * * * *